(12) United States Patent
Ying

(10) Patent No.: US 9,835,733 B2
(45) Date of Patent: Dec. 5, 2017

(54) APPARATUS FOR DETECTING X-RAYS

(71) Applicant: Zhengrong Ying, Belmont, MA (US)

(72) Inventor: Zhengrong Ying, Belmont, MA (US)

( * ) Notice: Subject to any disclaimer, the term of this patent is extended or adjusted under 35 U.S.C. 154(b) by 91 days.

(21) Appl. No.: 14/700,178

(22) Filed: Apr. 30, 2015

(65) Prior Publication Data

US 2016/0320495 A1 Nov. 3, 2016

(51) Int. Cl.
*G01T 1/20* (2006.01)

(52) U.S. Cl.
CPC ...... *G01T 1/2018* (2013.01); *G01N 2223/419* (2013.01); *G01N 2223/505* (2013.01); *G01T 1/2002* (2013.01)

(58) Field of Classification Search
CPC ............ G01T 1/2018; G01N 2223/419; G01N 2223/505; A61B 6/02; A61B 6/025; A61B 6/03; A61B 6/032; A61B 6/035
See application file for complete search history.

(56) References Cited

U.S. PATENT DOCUMENTS

| | | | |
|---|---|---|---|
| 6,426,991 B1 | 7/2002 | Mattson | |
| 6,522,715 B2 | 2/2003 | Hoffman | |
| 6,671,345 B2 | 12/2003 | Vrettos | |
| 7,606,346 B2 | 10/2009 | Tkaczyk | |
| 8,553,834 B2 | 10/2013 | Guery | |
| 8,710,448 B2* | 4/2014 | Luhta | G01T 1/2018 250/370.09 |
| 2007/0231970 A1* | 10/2007 | Fukuo | H01L 25/0657 438/127 |
| 2008/0011959 A1* | 1/2008 | Thorne | G01T 1/2018 250/370.09 |
| 2011/0158387 A1* | 6/2011 | Narayanaswamy | G01T 1/20 378/62 |
| 2012/0168632 A1* | 7/2012 | Yagi | A61B 6/4233 250/366 |
| 2016/0154124 A1* | 6/2016 | Luhta | H01L 27/14618 250/361 R |

* cited by examiner

*Primary Examiner* — Eliza Osenbaugh-Stewart

(57) ABSTRACT

An apparatus for detecting X-rays and converting the detected X-ray intensities into digital signals is disclosed. The apparatus places Analog to Digital Conversion (ADC) chips directly under a scintillator array along the X-ray beam direction and uses a shield that is placed between a photodiode substrate and an Analog to Digital Conversion (ADC) chip to block X-rays from directly reaching the dies of the ADC chips, which are sensitive to X-rays. Also an X-ray CT system utilizing the disclosed apparatus for detecting X-rays is provided.

12 Claims, 6 Drawing Sheets

APPARATUS FOR DETECTING X-RAYS

RELATED APPLICATIONS

This patent application is related to the following pending U.S. applications and/or issued U.S. patents, the contents of which are incorporated herein in their entirety by reference:

"Configurable data measurement and acquisition systems for multi-slice X-ray computed tomography systems," invented by Zhengrong Ying, U.S. application Ser. No. 13/589,245, filed on Aug. 20, 2012.

"Adjustable photon detection systems for multi-slice X-ray computed tomography systems," invented by Zhengrong Ying, U.S. application Ser. No. 13/760,127, filed on Feb. 6, 2013.

"Anti-scatter collimators for detector systems of multi-slice X-ray computed tomography systems," invented by Zhengrong Ying, U.S. application Ser. No. 13/908,897, filed on Jun. 3, 2013.

FIELD OF THE DISCLOSURE

The present disclosure relates to detecting and converting X-rays into digital signals with application related to X-ray Computed Tomography (CT) systems.

BACKGROUND OF THE DISCLOSURE

In X-ray CT systems, X-rays are used to image internal structures and features of a region of a subject or an object. The terms "subject" and "object" shall include anything capable of being imaged. The imaging is performed by an X-ray CT system, which images internal structures and features of a plurality of thin planar slices or a 3D volume of a region of an object using X-rays. For medical applications, the imaging objects include human bodies.

An X-ray CT system generally comprises an X-ray source that provides a cone-shaped X-ray beam and an array of closely spaced X-ray detectors that face the X-ray source. The X-ray source and the array of detectors are mounted in a gantry so that a patient being imaged with the CT system, generally lying on an appropriate support couch, can be positioned within the gantry between the X-ray source and the array of detectors. The gantry and the couch are moveable relative to each other so that the X-ray source and the detector array can be positioned axially at desired locations along the patient's body.

The gantry comprises a stationary structure referred to as a stator and a rotary element referred to as a rotor, which is mounted to the stator so that the rotor is rotatable about the axial direction. In third generation CT systems, the X-ray source and the array of detectors are mounted on the rotor. Angular positions of the rotor about the axial direction are controllable so that the X-ray source can be positioned at desired angles, referred to as view angles, around a patient's body.

To image a slice in a region of a patient's body, the X-ray source is positioned at an axial position of the slice and the X-ray source is rotated around the slice to illuminate the slice with X-rays from a plurality of different view angles. At each view angle, detectors in the array of detectors generate signals responsive to the intensity of X-rays from the source that passes through the slice. The signals are processed to determine the amounts, by which X-rays from the X-ray source are attenuated over various path lengths through the slice that the X-rays traverse, in passing though the slice from the X-ray source to the detectors. The amounts, by which the X-rays are attenuated, are used to determine the X-ray absorption coefficients of materials in the slice as a function of position in the slice. The absorption coefficients are used to generate an image of the slice and to identify compositions and densities of tissues in the slice.

The X-ray detectors comprised in a detector array of CT system are generally packaged in a plurality of modules, hereinafter referred to as detector modules, each of which comprises a plurality of X-ray detector elements. Most modern CT systems are multi-slice CT systems designed to simultaneously image a plurality of slices of a patient. The X-ray detector elements in each detector module of a multi-slice CT scanner are arranged in a matrix of rows and columns. The X-ray detector matrices of any two CT detector modules in a CT system are substantially identical and comprise a same number of rows of detector elements and a same number of columns of detector elements. The modules are positioned one adjacent to and contiguous with the other in a closely packed array with their rows of detectors aligned end to end so that the X-ray detector elements form a plurality of long parallel rows of X-ray detector elements.

A multi-slice X-ray CT system is usually named or featured by the maximum number of slices that it can simultaneously image, for example, an 8-slice CT system means that it can simultaneously image at most 8 slices; a 16-slice CT system can simultaneously image at most 16 slices.

The X-ray detector elements in each long row of the detector array lie on an arc of a circle having its center located at a focal point of the CT system's X-ray source, and the design of these detector elements and the detector modules is specifically determined by the radius of the circle, which is hereinafter referred to as focusing distance. The design of X-ray detector modules placed on the arc of one focusing distance of one CT system cannot therefore be used on another CT system of a different focusing distance.

Each detector element in a scintillator array is comprised of a finite active area for detecting X-ray photons and generating second-energy photons or electric charges when using X-ray direct conversion materials. Detector elements are surrounded by non-active areas, referred hereafter as gaps, which do not generate responses to X-ray photons.

An X-ray detector array typically includes an anti-scatter collimator having a plurality of anti-scatter plates for collimating X-ray beams received at each detector element: a scintillator for converting X-rays to light energy adjacent to the collimator, and a photodiode for receiving the light energy from the coupled scintillator and producing electric charges therefrom.

The electric charges generated from the detector array are then fed into Analog to Digital Conversion (ADC) Integrated Chips (ICs) to generate digital signals for processing and reconstructing tomographic images of scanned objects.

SUMMARY OF THE DISCLOSURE

In one embodiment of the present disclosure, an apparatus for detecting X-rays (hereinafter referred to as "detector module") is disclosed, comprising a scintillator array for receiving and converting incident X-ray photons to second energy light photons. Each X-ray scintillator array is divided into individual elements organized in a matrix fashion with element rows (Z-axis for row direction) and element columns (X-axis for column direction) for detecting X-ray photons. The individual scintillator elements are interspaced by gaps (areas that do not detect X-rays) and the X-ray photons are emitted from the positive Y-axis direction. The detector module further includes a photodiode module, onto which the X-ray scintillator array is mounted along the Y-axis, for converting the second energy light photons to electric charges, a photodiode substrate for mounting the photodiode module along the Y-axis, and one or more Analog to Digital Conversion (ADC) chips mounted on the photodiode substrate for converting the electric charges to digital signals. The ADC chips are mounted on the opposite side of the photodiode module and directly underneath the photodiode module along the Y-axis. The detector module may further include an X-ray shield that is placed between the photodiode substrate and each of the ADC chips for blocking X-ray photons attenuated by the individual scintillator elements and X-ray photons travelled through the gaps of the scintillator array from reaching the ADC chips. Since there is one shield for each ADC chip, the number of the shields equals to the number of the ADC chips.

In another embodiment of the present disclosure, an X-ray Computed Tomography (CT) system for generating CT images for objects to be imaged is also disclosed, comprising a rotatable gantry, an X-ray source mounted on the rotatable gantry for generating X-ray beams to pass through the objects, and a detector system mounted on the rotatable gantry to the opposite side of the X-ray source, for receiving the X-ray beams corresponding to the objects. The detector system may include a plurality of the detector modules as described previously.

BRIEF DESCRIPTION OF THE DRAWINGS

The drawing figures depict embodiments by way of example, not by way of limitation. In the figures, like reference numerals refer to the same or similar elements.

DETAILED DESCRIPTION OF THE DRAWINGS

Figure 1:
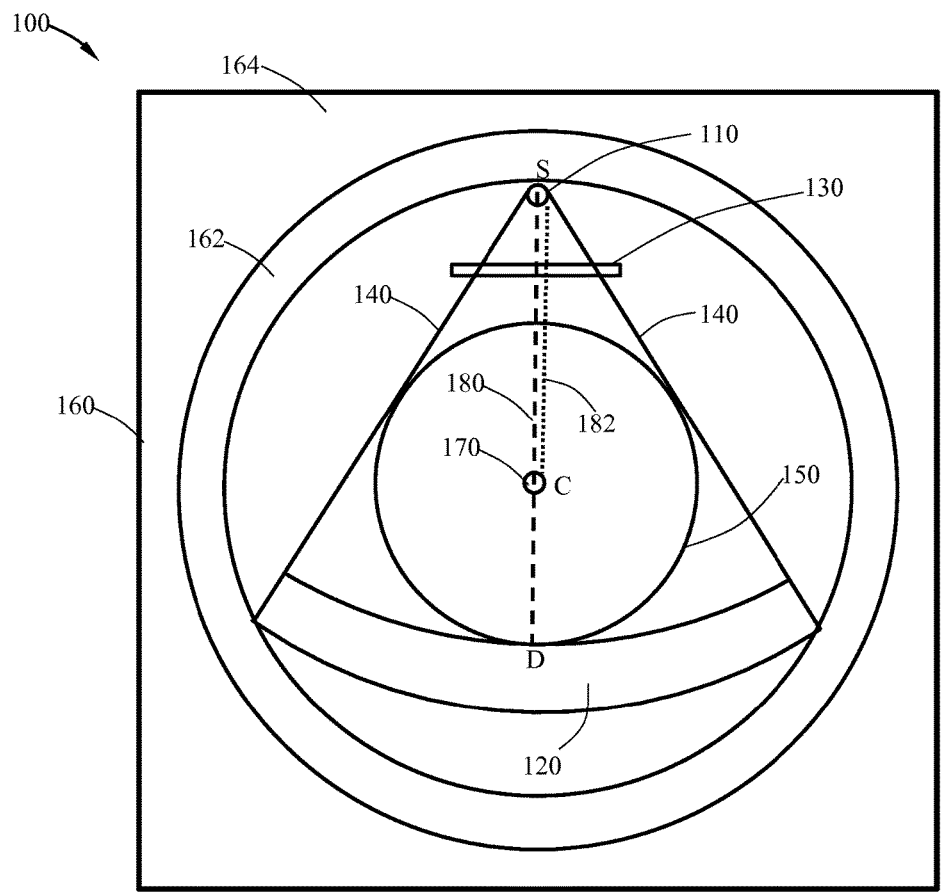
FIG. 1 illustrates a schematic functional diagram of a prior art multi-slice X-ray CT system.
Figure 1:
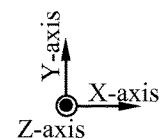

FIG. 1 shows a schematic functional diagram of a prior art multi-slice X-ray CT system 100. A multi-slice CT system typically comprises an X-ray source 110, which generates a cone-shaped X-ray beam 140. The X-ray beam 140 passes through a pre-patient collimator 130, which allows X-ray beam to illuminate only the targeted area and blocks X-ray beam in unwanted area. A patient usually lies down within the scanner's scanning Field Of View (FOV) 150, where the X-ray beam 140 illuminates. The X-ray detector system 120 receives X-ray photons and converts to analog signals that are proportional to X-ray photon energies. The X-ray CT system 100 also comprises a gantry 160, which includes a rotational part 162 and a stationary part 164. The X-ray source 110, the collimator 130 and the detector system 120 are mounted on the rotational part 162 of the gantry 160. The rotational part 162 rotates around the rotation center C 170.

The distance 182 between the focal spot S, which sometimes is interchangeably referred to as X-ray source position, of the X-ray source 110 and the rotation center C, which is interchangeably called iso-center, is hereinafter referred to as $R_{sc}$, and the distance 180 between the focal spot S of the X-ray source 110 and the detector system D is hereinafter referred to as focusing distance $R_{sd}$. Different CT systems may have different $R_{sc}$, $R_{sd}$, or/and scanning FOV.

The direction from the iso-center to the focal spot of the X-ray source is hereinafter referred to as Y-axis, and the direction perpendicular to the imaging plane or the rotation plane is hereinafter referred to as Z-axis, and the direction perpendicular to the Y-axis within the rotation plane is hereinafter referred to as X-axis.

Figure 2A:
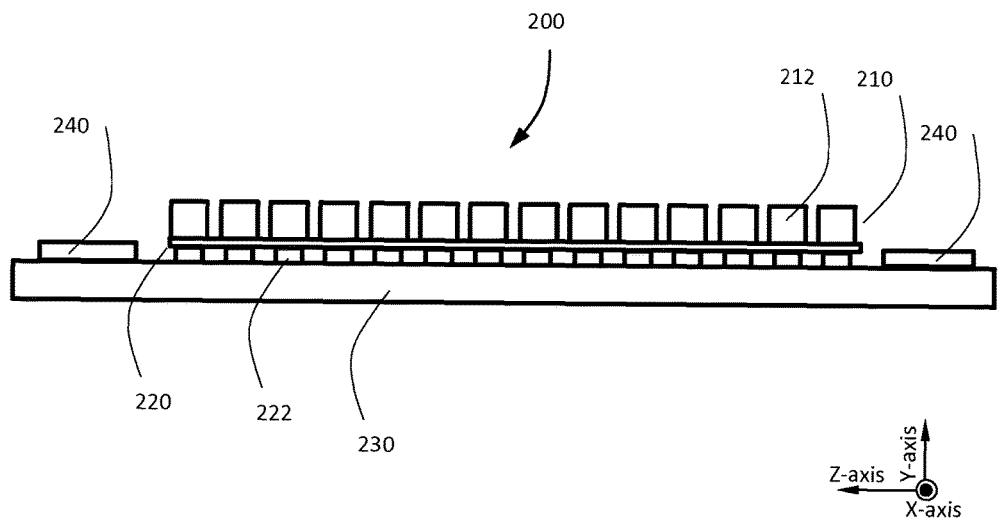
FIG. 2A illustrates a schematic diagram of a prior art detector module used in an X-ray CT system.
Figure 2B:
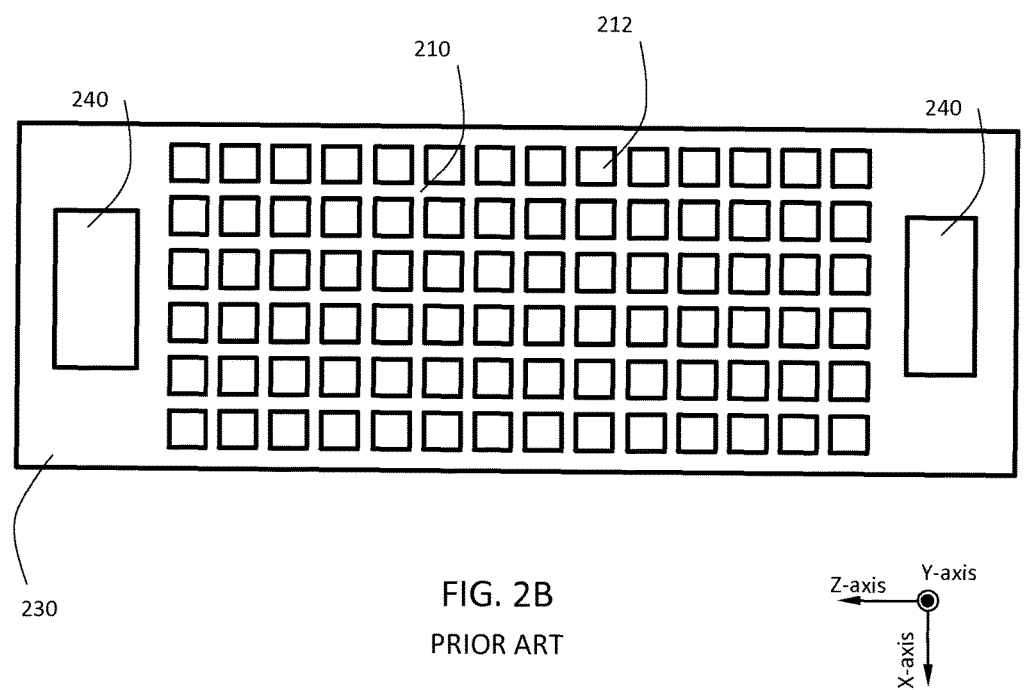
FIG. 2B shows a top view of the prior art detector module illustrated in FIG. 2A.

FIG. 2A illustrates a schematic diagram of a prior art detector module used in an X-ray CT system, and FIG. 2B shows the top view of the prior art detector module of FIG. 2A. A CT detector system is comprised of many detector modules 200 placed side by side along an arced support structure (not shown). Each detector module comprises a scintillator array 210, a photodiode module 220, a photodiode substrate 230, and a plurality of Analog to Digital Conversion (ADC) chips 240. The detector module 200 is placed in the X-Y-Z coordinate system as defined previously: the X-ray beam (not shown) comes from the positive Y-axis direction, and the detector module is placed in X-Z plane to receive the X-ray beam coming from the positive Y-axis direction.

Referring to FIG. 2A and FIG. 2B, the scintillator array 210 is divided into individual scintillator elements 212 in a matrix fashion with rows and columns. The row direction is along the Z-axis and the column direction is along the X-axis. The distances between the centers of two neighboring elements are referred to as pitch. The pitch along the X-axis is called X-pitch and the pitch along the Z-axis is called Z-pitch. Each scintillator element 201 receives X-ray photons and converts into second energy light photons. The individual scintillator elements 201 are interspaced by gaps that do not detect X-ray photons. The gaps are usually filled with materials that do not attenuate X-ray as much as individual scintillator elements.

Still referring to FIG. 2A and FIG. 2B, the scintillator array 210 is mounted on the top of the photodiode module 220, where the term "top" is defined as a relationship of one object being more positive than another object along the Y-axis. The photodiode module is also divided into a matrix of photodiode elements with same X-pitch and Z-pitch as those within the scintillator array. The second light photons, which are typically visible light photons generated by each individual scintillator element, are received by each individual photodiode element and are converted to electric charges.

Still referring to FIG. 2A and FIG. 2B, the electric charges generated by each individual photodiode element are transported by conductors like traces and vias (not shown) in the photodiode substrate 230 to Analog to Digital Conversion (ADC) chips 240 to be converted into digital signals.

The ADC chips are sensitive to X-rays, thus are not placed directly under the scintillator array as shown in FIG. 2A and FIG. 2B. Instead, the ADC chips are placed at the ends of detector module 200, because the gaps in the scintillator array do not absorb enough X-ray photons and also there are some remaining X-ray photons after being attenuated by the individual scintillator elements. The term "under" is defined as a relationship of an object being more negative than another object along the Y-axis. The term "ends" or "end" is along the both or either directions of the Z-axis.

Placing the ADC chips at the end or ends of a detector module does not allow the detector modules to be tiled side by side along four directions (tileable). The prior art detector module 200 as shown in FIG. 2A and FIG. 2B can be placed side by side along the X-axis, but cannot be placed side by side along the Z-axis to form a larger 2D matrix for a detector system to receive a continuous wide X-ray beam along the Z-axis. The continuous wide X-ray beam would strike the ADC chips placed at the ends of each detector module along the Z-axis, deteriorating the performance or evening damaging the functions of the ADC chips.

Figure 3:
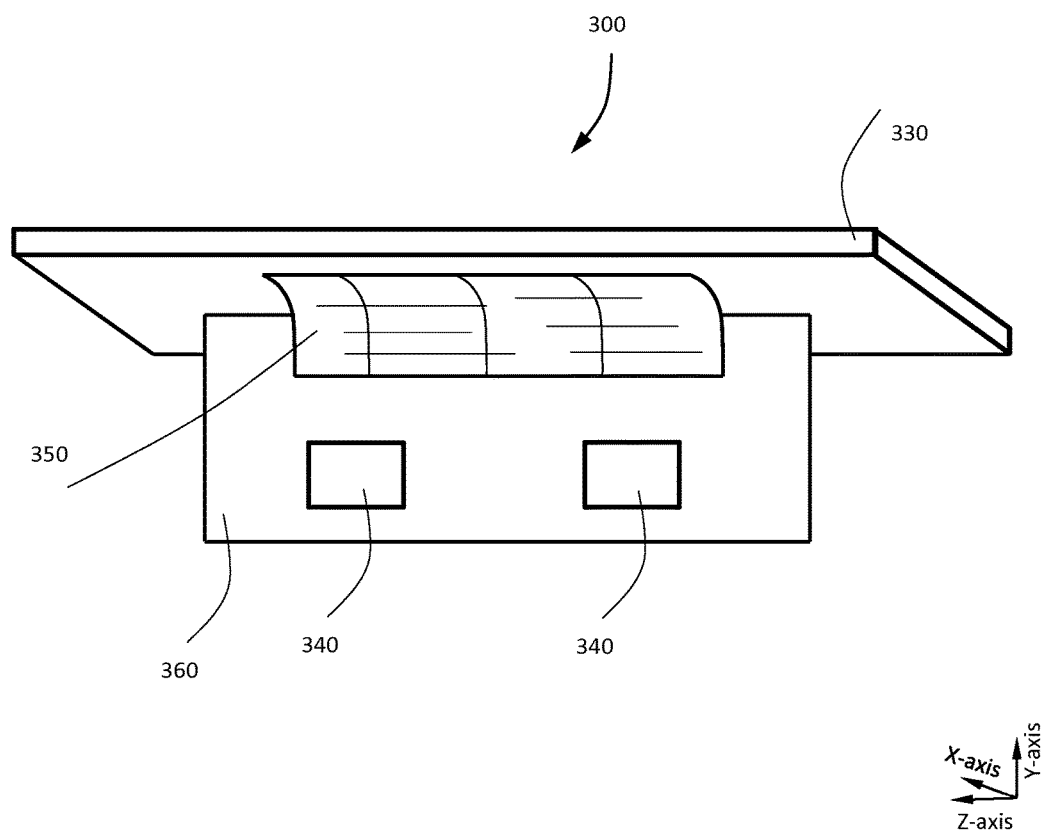
FIG. 3 illustrates a schematic diagram of a prior art detector module used in an X-ray CT system.

FIG. 3 illustrates a schematic diagram of a prior art detector module 300 used in an X-ray CT system. In order to overcome the non-tileable limitation of the detector modules depicted in FIG. 2A and FIG. 2B, the prior art detector module 300 shown in FIG. 3 uses a flex print circuit 350 to electrically connect the outputs of the photodiode module (not shown) through the photodiode substrate 330 to ADC board 360, onto which the ADC chips 340 are soldered. The ADC board 360 and the ADC chips 340 are typically perpendicular or close to perpendicular to the photodiode substrate 330 so as to minimize the area on the ADC chips for receiving X-ray photons. As stated previously that the ADC chips are sensitive to the X-rays, excessive exposure to the X-rays may deteriorate the performance and even damage the functionality of the ADC chips. The flex printed circuit 350 and the ADC board 360 might be combined using a flex rigid printed circuit, however the design and manufacturing of the flex or flex rigid printed circuit is still costly nowadays.

Figure 4A:
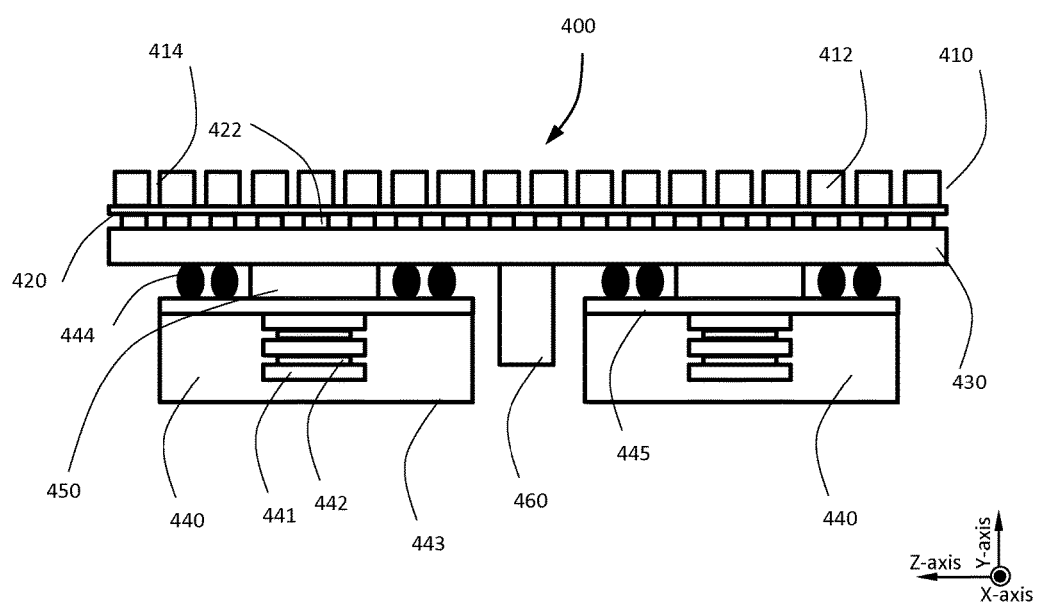
FIG. 4A illustrates a schematic diagram of an X-ray detector module in accordance with one embodiment of the present disclosure.
Figure 4B:
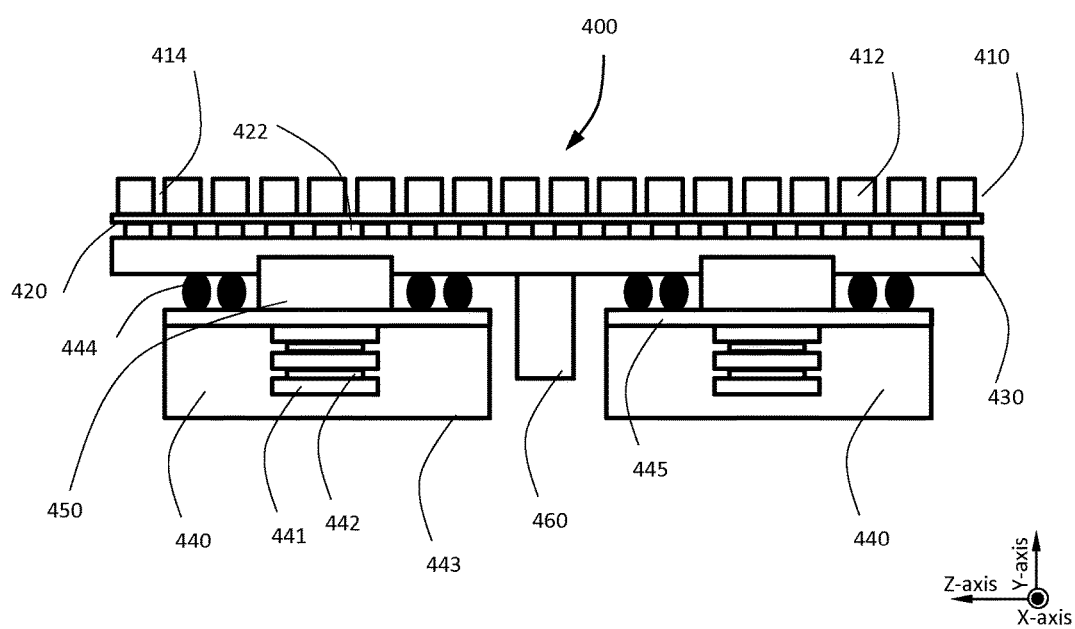
FIG. 4B illustrates a schematic diagram of an X-ray detector module in accordance with one embodiment of the present disclosure.

FIG. 4A illustrates a schematic diagram of an X-ray detector module in accordance with one embodiment of the present disclosure. FIG. 4B illustrates another schematic diagram of an X-ray detector module in accordance with another embodiment of the present disclosure. The detector module 400 may be tileable among the four directions: along X-axis and Z-axis. The detector module 400 comprises a scintillator array 410, a photodiode module 420, a photodiode substrate 430, a plurality of Analog to Digital Conversion (ADC) chips 440, a plurality of shields 450, and one or more digital connectors 460. The scintillator array 410 is divided into individual scintillator elements 412 in a matrix fashion with rows and columns. The scintillator array 410 is mounted directly on top of the photodiode module 420 along the Y-axis as shown in FIG. 4A and FIG. 4B.

In one aspect of the present disclosure, there may be small glasses balls (not shown) placed between the scintillator array 410 and the photodiode module 420 to improve the efficiency of the light transfer from the scintillator array 410 to the photodiode module 420; an example diameter of these glass balls is 50 um.

In another aspect of the present disclosure, the gaps 414 within the scintillator array 410 are filled with light reflective coating materials including at least, for example, titanium dioxide, titanium oxide, or tungsten oxide material. The light reflective coating is to prevent the generated second energy light photons from being escaped in unwanted directions.

In one embodiment of the present disclosure, the photodiode module 420 is mounted on top of the photodiode substrate 430. The photodiode module 420 may be electrically connected with the photodiode substrate 430 using soldering process, such as reflow process, to solder the photodiode module 420 to the photodiode substrate 430. Each individual scintillator element receives X-ray photons and generates the second light photons, for an example, light spectrum with peak light wavelength at 510 nm. The second light photons are blocked by the reflective coating at the scintillator array 410 except the interface to the photodiode module 420. Each photodiode element 422 receives the light photons from the corresponding scintillator element 412 and converts the received light photons to electric charges.

In one embodiment of the present disclosure, the Analog to Digital Conversion (ADC) chips 440 are directly mounted onto the photodiode substrate 430 on the opposite side of the photodiode module 420 and directly under the scintillator array 410. Because the ADC chips 440 are directly under the scintillator array 410, the ADC chips 440 are subject to the exposure of the X-ray beam striking at the scintillator array 410 from the positive direction of the Y-axis: the X-ray photons attenuated by individual scintillator elements 412 and the ones penetrated through the gaps 414 of the scintillator array 410.

In one embodiment of the present disclosure, the ADC chip 440 comprises a plurality of dies 441, a plurality of die spacer 442, an ADC substrate 445, an ADC lid 443 and a plurality of solder balls 444. In one aspect of the embodiment of the present disclosure, all the dies 441 of an ADC chip are identical or substantially identical in terms of function and dimensions. Each die is made of semiconducting materials to perform the processing needed to convert the input electric charges to digital signals, and the dies 441 are the only X-ray sensitive part within the ADC chip 440. For example, a die with about 10 mm along the X-axis and about 10 mm along Z-axis in dimensions has 128 analog inputs and simultaneously converts the input analog signals to digital signals, and the digital output of each conversion of each analog input is 24 bits. In another aspect of the embodiment of the present disclosure, the dies 441 are stacked together along the Y-axis in order to reduce the X-Z dimensions for the ADC chip 440. The die spacers 442 are used to adhere the neighboring dies together, examples of the die spacers include but not limited to die attach paste and die attach film.

In an exemplary configuration of the detector module 400, there are three dies 441 stacked together with 128 analog inputs for each die, resulting in total of 384 inputs for one ADC chip 440; the scintillator array 410 and the photodiode module 420 are of 32 rows along the Z-axis and 24 columns along the X-axis, resulting in total of 768 analog inputs, and each detector module 400 contains 2 ADC chips.

In another embodiment of the present disclosure, the ADC substrate 445 provides the base for the stacked dies 441 and as well as the electrical interface between the dies 441 and the solder balls 444. The electrical connections between the dies 441 and the ADC substrate 445 use, for an example, wire-bond (not shown) technique. The solder balls 444 provide electrical connections and mechanical bonding between the photodiode substrate 430 and the ADC chip 440.

In yet another embodiment of the present disclosure, the analog signals (electric charges) generated from each individual photodiode element 422 are transported to each input of the ADC chip 440, and processed at the corresponding dies 441; the converted digital signals of all or some of the inputs are outputted serialized to a few solder balls to be transported to the digital connector 460. The digital connector 460 serves as an electrical interface of the detector module 400.

In another embodiment of the present disclosure, a shield 450 is placed between the photodiode substrate 430 and each ADC chip 440 as shown in FIG. 4A and FIG. 4B. The shield 450 is not part of the photodiode substrate 430 or part of the ADC 440. The shield 450 is made of high Z materials, such as tungsten or tungsten alloy with at least twenty percent of tungsten concentration, to absorb or block X-ray photons. The shield 450 is placed on top of the ADC chip 440 so that the dies 441 of the ADC chip 440 are completed covered by the shield 450 so that the X-ray photons attenuated and penetrated through the scintillator array 410 are blocked by the shield 450 and may not reach the X-ray sensitive dies 441 of the ADC chip 440. For example, the dies 441 of the ADC chip 440 are of size of 10 mm by 10 mm along the X-axis and Z-axis, and the shields 450 are of size of 11 mm by 11 mm along the X-axis and Z-axis; each shield 450 and each ADC chip 440 are aligned so that no X-rays emitted from positive Y-axis direction striking at the scintillator array 410 can reach the dies 441 of the ADC chip 440 directly.

In another embodiment of the present disclosure, the thickness of the shields 450 is slightly less than the height of the solder balls 444 of the ADC chips as shown in FIG. 4A. The height of the solder balls is defined as the solder ball height along the Y-axis between the ADC substrate 445 and the photodiode substrate 430. The thickness constraint on the shields 450 is to allow the shield 450 and the solder balls 444 to be placed in the same range along the Y-axis and completely sandwiched between the ADC chip 440 and the photodiode substrate 430. In one exemplary embodiment of the present disclosure, the solder ball height is about 0.5 mm, and the thickness of the shield 450 is about 0.35 mm.

In another embodiment of the present disclosure, a thermal insulation layer such as thermal insulation paste is placed between the ADC chip 440 and the shield 450 so that the heat generated by the ADC chip 440 may not be transferred to the photodiode module 420 easily as the photodiode module 420 is temperature sensitive in terms of performance. The heat generated by the ADC chips 440 may be dissipated along the direction toward the ADC lid 443 by air ventilation.

Yet in another embodiment of the present disclosure, the photodiode substrate 430 may have portions recessed from the negative Y-axis direction so that each shield 450 can be placed within the recessed area of the photodiode substrate 430 as shown in FIG. 4B. With the recessed photodiode substrate 430, the thickness of the shield may not have to be smaller than the height of the solder balls 444 of the ADC chips 440.

Figure 4C:
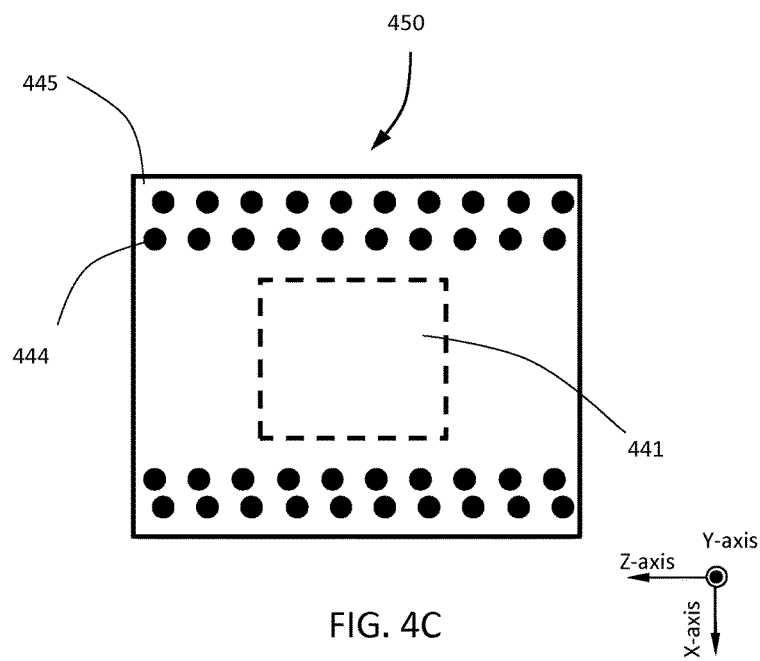
FIG. 4C illustrates a schematic diagram of an Analog to Digital Conversion (ADC) chip in accordance with one embodiment of the present disclosure.

FIG. 4C illustrates a schematic diagram of an Analog to Digital Conversion (ADC) chip in accordance with one embodiment of the present disclosure. A plurality of the solder balls 444 are placed on the ADC substrate 445 surrounding the dies 441, but not overlapping on top of the dies 441 along the Y-axis. The opening area for the dies 441 in the ADC substrate 445 is needed in order to place the shield 450 as shown in FIG. 4A and FIG. 4B to block the X-rays from reaching the dies 441. The solder balls 444 can be placed on all of the four sides of the dies 441, at three sides of the dies 441, two sides of the dies 441, or even one side of the dies 441 within the X-Z plane.

Still referring to FIG. 4A, FIG. 4B, and FIG. 4C, in one embodiment of the present disclosure, each shield 450 for each ADC chip 440 is confined and enclosed by the solder balls 444 of the ADC chip 440, and is completely sandwiched by the ADC chip 440 and the photodiode substrate 430 without the shield 450 protruding outside each ADC chip 440 in any direction within the X-Z plane.

Figure 4D:
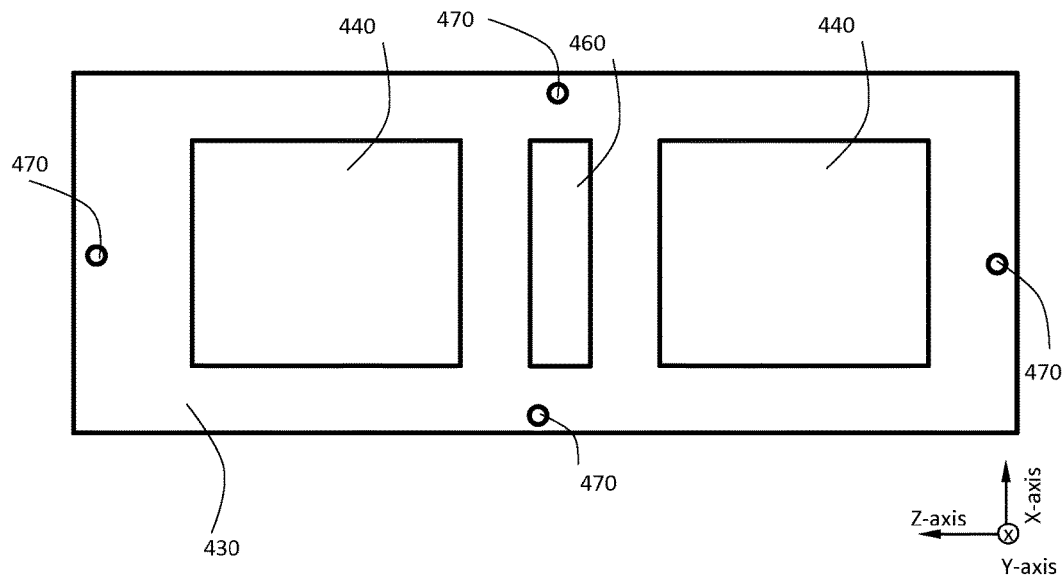
FIG. 4D illustrates a schematic diagram of a photodiode substrate layout in accordance with one embodiment of the present disclosure.

FIG. 4D illustrates a schematic diagram of a photodiode substrate layout in accordance with one embodiment of the present disclosure. The locating holes 470 are placed on the bottom side (negative Y-axis side, where the ADC chips are mounted on) of photodiode substrate 430 for referencing the detector module 400 to be aligned and assembled in a detector system of a CT system. The locating holes are half-blind holes, and not through holes to the top side (positive Y-axis side, where the photodiode module is mounted on) of the photodiode substrate 430. There are at least two locating holes 470 at each of the photodiode substrate 430.

In another embodiment of the present disclosure, an X-ray Computed Tomography (CT) system for generating CT images for objects to be imaged comprises a rotatable gantry, an X-ray source mounted on the rotatable gantry for generating X-ray beams to pass through the objects; and a detector system mounted on the rotatable gantry to the opposite side of the X-ray source, for receiving the X-ray beams corresponding to the objects. The detector system includes a plurality of detector modules and each of the detector modules comprises a scintillator array for receiving and converting incident X-ray photons to second energy light photons. Each X-ray scintillator array is divided into individual elements organized in a matrix fashion with element rows (Z-axis for row direction) and element columns (X-axis for column direction) for detecting X-ray photons. The individual scintillator elements are interspaced by gaps (areas that do not detect X-rays) and the X-ray photons are emitted from the positive Y-axis direction. The detector module further includes a photodiode module, onto which the X-ray scintillator array is mounted along the Y-axis, for converting the second energy light photons to electric charges, a photodiode substrate for mounting the photodiode module along the Y-axis, and one or more Analog to Digital Conversion (ADC) chips mounted on the photodiode substrate for converting the electric charges to digital signals. The ADC chips are mounted on the opposite side of the photodiode module and directly underneath the photodiode module along the Y-axis. The detector module may further include an X-ray shield that is placed between the photodiode substrate and each of the ADC chips for blocking X-ray photons attenuated by the individual scintillator elements and X-ray photons travelled through the gaps of the scintillator array from reaching the ADC chips. Since there is one shield for each ADC chip, the number of the shields equals to the number of the ADC chips.

While this disclosure has been particularly shown and described with references to the embodiments thereof, it will be understood by those skilled in the art that various changes in forms and details may be made therein without departing from the spirit and scope of the disclosure as defined by the following claims.

The invention claimed is:

1. An apparatus for detecting X-rays comprising:
   A. A scintillator array for receiving and converting incident X-ray photons to second energy light photons; wherein each said X-ray scintillator array is divided into individual elements organized in a matrix fashion with element rows (Z-axis for row direction) and element columns (X-axis for column direction) for detecting X-ray photons; wherein said individual scintillator elements are interspaced by gaps (areas that do not detect X-rays); wherein the X-ray photons are emitted from the positive Y-axis direction;

B. A photodiode module, onto which said X-ray scintillator array is mounted along the Y-axis, for converting said second energy light photons to electric charges;

C. A photodiode substrate for mounting said photodiode module along the Y-axis;

D. One or more Analog to Digital Conversion (ADC) chips mounted on said photodiode substrate for converting said electric charges to digital signals; wherein said ADC chips are mounted on the opposite side of said photodiode module and directly underneath said photodiode module along the Y-axis; wherein each said ADC chip comprising:
  i. One or more stacked identical or substantially identical dies along the Y-axis;
  ii. An ADC substrate for said dies to be stacked on along the Y-axis; and
  iii. A plurality of solder balls are placed on said ADC substrate not overlapped with said dies along the Y-axis;
  wherein said dies and said solder balls are mounted not on the same side but on the opposite sides of said ADC substrate; wherein said solder balls of said ADC chips are directly soldered to said photodiode substrate to be electrically connected to said photodiode module to transport said electric charges generated by said photodiode module directly to said ADC chips for conversion;

E. An X-ray shield is placed between said photodiode substrate and each of said ADC chips for blocking X-ray photons attenuated by said individual scintillator elements and X-ray photons travelled through said gaps of said scintillator array from reaching said ADC chips; wherein said shields and said solder balls of ADC chips are not overlapped along the Y-axis; wherein the number of said shields equals to the number of said ADC chips; and, F. A digital connector mounted on said photodiode substrate.

2. The apparatus of claim 1, wherein said X-ray shields are plates made of tungsten or tungsten alloy with tungsten concentration no less than twenty percent.

3. The apparatus of claim 1, wherein a thermal insulation layer is placed between each of said shields and each of said ADC chips to insulate the heat generated by said ADC chips from reaching said photodiode module directly.

4. The apparatus of claim 1, wherein the X-Z dimensions of each of said X-ray shields are larger than said dies of said ADC chips to block X-rays from reaching said dies of said ADC chips directly.

5. The apparatus of claim 1, wherein the thickness of said X-ray shields is smaller than the height of said solder balls of said ADC chips along the Y-axis.

6. The apparatus of claim 5, wherein the thickness of said X-ray shields is no greater than 0.5 mm.

7. The apparatus of claim 1, wherein there are three dies in each of said ADC chips; wherein each die converts 128 analog inputs to digital signals and each ADC chip converts 384 analog inputs to digital signals.

8. The apparatus of claim 7, wherein said scintillator array has 32 rows and 24 columns; wherein there are two ADC chips mounted on said photodiode substrate.

9. The apparatus of claim 1, wherein a plurality of portions of the side of said photodiode substrate on which said ADC chips are mounted on are recessed along the Y-axis to have a portion of each of said shields along the Y-axis to be placed inside said recessed areas of said photodiode substrate.

10. An X-ray Computed Tomography (CT) system for generating CT images for objects to be imaged comprising:
A. A rotatable gantry;
B. An X-ray source mounted on said rotatable gantry for generating X-ray beams to pass through said objects; and,
C. A detector system mounted on said rotatable gantry to the opposite side of said X-ray source, for receiving said X-ray beams corresponding to said objects; wherein said detector system comprises a plurality of detector modules; wherein each of said detector modules comprising:
  i. A scintillator array for receiving and converting incident X-ray photons to second energy light photons; wherein each said X-ray scintillator array is divided into individual elements organized in a matrix fashion with element rows (Z-axis for row direction) and element columns (X-axis for column direction) for detecting X-ray photons; wherein said individual scintillator elements are interspaced by gaps (areas that do not detect X-rays); wherein the X-ray photons are emitted from the positive Y-axis direction;
  ii. A photodiode module, onto which said X-ray scintillator array is mounted along the Y-axis, for converting said second energy light photons to electric charges;
  iii. A photodiode substrate for mounting said photodiode module along the Y-axis;
  iv. One or more Analog to Digital Conversion (ADC) chips mounted on said photodiode substrate for converting said electric charges to digital signals; wherein said ADC chips are mounted on the opposite side of said photodiode module and directly underneath said photodiode module along the Y-axis; wherein each said ADC chip comprising:
    1. One or more stacked identical or substantially identical dies along the Y-axis;
    2. An ADC substrate for said dies to be stacked on along the Y-axis; and
    3. A plurality of solder balls are placed on said ADC substrate not overlapped with said dies along the Y-axis;
    wherein said dies and said solder balls are mounted not on the same side but on the opposite sides of said ADC substrate; wherein said solder balls of said ADC chips are directly soldered to said photodiode substrate to be electrically connected to said photodiode module to transport said electric charges generated by said photodiode module directly to said ADC chips for conversion;
  v. An X-ray shield is placed between said photodiode substrate and each of said ADC chips for blocking X-ray photons attenuated by said individual scintillator elements and X-ray photons travelled through said gaps of said scintillator array from reaching said ADC chips; wherein said shields and said solder balls of ADC chips are not overlapped along the Y-axis; wherein the number of said shields equals to the number of said ADC chips; and
  vi. A digital connector mounted on said photodiode substrate.

11. An apparatus for detecting X-rays comprising:
A. A scintillator array for receiving and converting incident X-ray photons to second energy light photons; wherein each said X-ray scintillator array is divided into individual elements organized in a matrix fashion with element rows (Z-axis for row direction) and element columns (X-axis for column direction) for detecting X-ray photons; wherein said individual scintillator elements are interspaced by gaps (areas that do not detect X-rays); wherein the X-ray photons are emitted from the positive Y-axis direction;

B. A photodiode module, onto which said X-ray scintillator array is mounted along the Y-axis, for converting said second energy light photons to electric charges;

C. A photodiode substrate for mounting said photodiode module along the Y-axis;

D. One or more Analog to Digital Conversion (ADC) chips mounted on said photodiode substrate for converting said electric charges to digital signals; wherein said ADC chips are mounted on the opposite side of said photodiode module and directly underneath said photodiode module along the Y-axis; wherein each said ADC chip comprising:
  i. One or more stacked identical or substantially identical dies along the Y-axis;
  ii. An ADC substrate for said dies to be stacked on along the Y-axis; and,
  iii. A plurality of solder balls are placed on said ADC substrate;
  wherein said dies and said solder balls are mounted not on the same side but on the opposite sides of said ADC substrate; wherein said solder balls of said ADC chips are directly soldered to said photodiode substrate to be electrically connected to said photodiode module to transport said electric charges generated by said photodiode module directly to said ADC chips for conversion;

E. An X-ray shield is placed between said photodiode substrate and said dies of each of said ADC chips for blocking X-ray photons attenuated by said individual scintillator elements and X-ray photons travelled through said gaps of said scintillator array from reaching said dies of said ADC chips; and, F. A digital connector mounted on said photodiode substrate.

12. The apparatus of claim 11, wherein each said shield is placed between each of said ADC substrates and said dies of each of said ADC chips.

* * * * *